US012741985B2

(12) United States Patent
Suresh Babu et al.

(10) Patent No.: US 12,741,985 B2
(45) Date of Patent: Sep. 22, 2026

(54) PROCESS FOR ISOLATION OF SAPONINS UTTROSIDE B AND UTTROSIDE A FROM SOLANUM NIGRUM LINN

(71) Applicant: COUNCIL OF SCIENTIFIC AND INDUSTRIAL RESEARCH AN INDIAN REGISTERED BODY INCORPORATED UNDER, New Delhi (IN)

(72) Inventors: Katragadda Suresh Babu, Hyderabad (IN); Bandi Siva, Hyderabad (IN); Kummari Narender, Hyderabad (IN); Halmathur Mahabalarao Sampath Kumar, Hyderabad (IN)

(73) Assignee: COUNCIL OF SCIENTIFIC AND INDUSTRIAL RESEARCH AN INDIAN REGISTERED BODY INCORPORATED UNDER THE REGN. OF SOC. ACT (ACT XX1 OF 1860), New Delhi (IN)

( * ) Notice: Subject to any disclaimer, the term of this patent is extended or adjusted under 35 U.S.C. 154(b) by 0 days.

(21) Appl. No.: 18/547,998

(22) PCT Filed: May 15, 2023

(86) PCT No.: PCT/IN2023/050453

§ 371 (c)(1),
(2) Date: Aug. 25, 2023

(87) PCT Pub. No.: WO2023/223345

PCT Pub. Date: Nov. 23, 2023

(65) Prior Publication Data

US 2025/0074936 A1 Mar. 6, 2025

(30) Foreign Application Priority Data

May 17, 2022 (IN) ............................ 202211028459

(51) Int. Cl.
*C07J 71/00* (2006.01)

(52) U.S. Cl.
CPC ................................ *C07J 71/0005* (2013.01)

(58) Field of Classification Search
CPC ......................... C07J 71/0005; A61K 31/7048
See application file for complete search history.

(56) References Cited

FOREIGN PATENT DOCUMENTS

| | | |
|---|---|---|
| IN | 201811042595 A | 5/2020 |
| WO | WO 2017208254 A1 | 12/2017 |

OTHER PUBLICATIONS

Majinda (2012) “Extraction and Isolation of Saponins,” pp. 415, in Natural Products Isolation, Methods in molecular Biology, vol. 864. (Year: 2012).*

Guo et al., “Optimization of Ethanol Extraction Process of Solanum nigrum Linn. and Structural Confirmation of its Compounds,” Asian Journal of Chemistry, Jul. 16, 2014, 26(15):4615-4618.

Hu et al., “Antineoplastic agents III: Steoridal Glycosides from Solanum nigrum,” Planta Med, 1999, 65:35-38.

Ikeda et al., “Cytotoxic Activity of Steroidal Glycosides from Solanum Plants,” Chem. Pharm. Bull., 2003, 26(8):1198-1201.

Ikeda et al., “Steroidal Oligoglycosides from Solanum Nigrum,” Chem. Pharm. Bull., 2000, 48:1062-1064.

Jain et al., “Solanum nigrum: Current Perspectives on Therapeutic Properties,” J. Clin. Ther., 2011, 16(1):78-85.

Jin et al., “Spirostanol and Furostanol Glycosides from the Fresh Tubers of Polianthes tuberosa,” J. Nat. Prod., 2004, 67:5-9.

Lai et al., “Anti-Cancer Activity of Solanum nigrum (AESN) through Suppression of Mitochondrial Function and Epithelial-Mesenchymal Transition (EMT) in Breast Cancer Cells,” Molecules, 2016, 11 pages.

Li et al., “Rapid structural characterization of triterpenoid saponins in crude extract from Symplocos chinensis using liquid chromatography combined with electrospray ionization tandem mass spectrometry,” Journal of Chromatography A, Jan. 6, 2006, pp. 53-62.

Lin et al., “Hepatoprotective effects of Solanum nigrum Linn extract against CC14-iduced oxidative damage in rats,” Chemico-Biological Interactions, 2008, 171:283-293.

Ma et al., “Study on chemical components of steroidal saponins from *Tribulus terrestris* L.,” J. Tianjin Univ. Trad. Chin. Med., 2012, 2 pages.

Nath et al., “Evaluation of uttroside B, a saponin from Solanum nigrum Linn, as a promising chemotherapeutic agent against hepatocellular carcinoma”, Scientific Reports, Nov. 3, 2016, 6:36318, 13 pages.

qbiomed.com [online], “Q BioMed’s Uttroside-B Receives U.S. FDA Orphan Drug Designation in the Treatment of Liver Cancer,” Jan. 27, 2021, retrieved on Aug. 16, 2023, retrieved from URL<https://qbiomed.com/news-and-media/news-2021/212-q-biomed-s-uttroside-b-receives-u-s-fda-orphan-drug-designation-in-the-treatment-of-liver-cancer>, 4 pages.

Särkinen et al., “A revision of the Old World Black Nightshades (Morelloid clade of *Solanum* L., *Solanaceae*), ” PhytoKeys 2018, 106:1-223.

Sharma et al., “Oligofurostanosides from Solanum Nigrum,” Phytochemistry, 1983, 22(5):1241-1244.

Zhao et al., “Solanum steroidal glycoalkaloids: structual diversity, biological activities, and biosynthesis,” Natural Product Reports, Oct. 1, 2020, 22 pages.

Zhou et al., “Steroidal Saponins from Solanum nigrum,” J. Nat. Prod., 2006, 69:1158-1163.

* cited by examiner

*Primary Examiner* — Layla D Berry
(74) *Attorney, Agent, or Firm* — Fish & Richardson P.C.

(57) ABSTRACT

The present invention relates to an improved and economical process for isolation of saponins, uttroside B and uttroside A from the whole plant of *Solanum nigrum* using a simple precipitation and without the use of any preparative HPLC purification step.

9 Claims, No Drawings

PROCESS FOR ISOLATION OF SAPONINS UTTROSIDE B AND UTTROSIDE A FROM SOLANUM NIGRUM LINN

FIELD OF THE INVENTION

The present invention relates to an improved and economical process for isolation of saponins, uttroside B and uttroside A from the whole plant of *Solanum nigrum.*

BACKGROUND OF INVENTION

Saponins, a group of plant secondary metabolites referred as triterpene/steroidal glycosides have attracted considerable attention from medicinal chemists as well as chemical biologists because of their fascinating structural diversity and important biological activities (Zhao, D-K et. al., Nat. Prod. Rep. 2020, 38, 1423-1444). *Solanum nigrum* is a herbaceous plant with small rounded berry fruits (family: Solanaceae) which is commonly known as black nightshade (Särkinen, T et. al., PhytoKeys 2018, 106, 1-223). It has been widely used in the Indian traditional systems of medicine and believed to have various pharmacological activities (Jain, R et. al., J. Clin. Ther. 2011, 16, 78-85). It is used as a hepatoprotective agent (Lin, H. M et. al., Chem.-Biol. Interact. 2008, 171, 283-293) and also for the treatment of various kinds of tumours (Lai, Y-J et. al., Molecules 2016, 21, 553), including liver cancer, breast cancer, stomach cancer and colon cancer. Alcoholic extract of the whole plant *S. nigrum* has been reported to induce cytotoxicity in different cancer cell lines (Hu, K et. al., Planta Med. 1999, 65, 35-38: Zhou, X et. al., J. Nat. Prod. 2006, 69, 1158-1163). Steroidal saponins, steroidal alkaloids, and steroidal oligoglycosides, including solamargine, solasonine, solavilline, solasdamine, and solanine are by far the most abundant metabolites of this plant extract (Ikeda, T et. al., Chem. Pharm. Bull. (Tokyo) 2000, 48, 1062-1064).

In particular, uttroside B and uttroside A are the potent steroidal saponins reported from this plant which displayed cytotoxicity towards PC-12 ($IC_{50}$ 1.20 μM), HCT-16 ($IC_{50}$ 2.33 μM) and moderate cytotoxicity ($IC_{50}$ 15.43 μM) against HeLa cells, respectively (Jin, J.-M et. al., J. Nat. Prod. 2004, 67, 5-9; Ikeda, T. et al., Chem. Pharm. Bull. 2003, 26, 1198-1201). Structurally, Uttroside B is characterized by the presence of β-D-glucopyranosyl unit at C-26 of the furostanol and β-lycotctraosyl unit at C-3 while uttroside A structurally differs from uttroside B by just one methoxyl group at C-22. The compound, uttroside B has also been isolated from the other species, *Tribulus terrestris* (Wu, K.-L et al., J. Tianjin Univ. Trad. Chin. Med. 2012, 31, 225-228) and Polianthes tuberose (Jin, J.-M et al., J. Nat. Prod. 2004, 67, 5-9).

The complex molecular architecture and potent biological activities of both uttroside A and uttroside B has stimulated considerable interest from chemists and biologists from the time of its isolation. Subsequently, few reports are available in the literature for the isolation and biological studies of uttroside B and uttroside A. Sharma et. al. have reported two furostanol saponins, uttroside A and B, from the methanolic extract of the stems and roots of *S. nigrum* and also reported their interconvertibility in refluxing with methanol and acetone, respectively (Sharma, S. C et al., Phytochemistry. 1983, 22, 1241-1244). Guo et. al reported the optimization of ethanolic extract of *Solanum nigrum* and isolation of its constituents including uttroside A and uttroside B (Guo, S-B et al., Asian Journal of Chemistry 2014, 26(15), 4615-4618). Recently, John Anty et al. reported and filed a patent application [International Publication Number WO 2017/208254 A1] regarding potential activity of uttroside B towards Hep-G2 cells (Nath, L. R et al., Scientific Reports 2016, 6, 36318). Halmuthur et al reported the adjuvant activities of uttroside A and B [201811042595]. Very recently, US FDA has approved the uttrosdie B as an orphan drug (Q BioMed's uttroside-b receives U.S. FDA orphan drug designation in the treatment of liver cancer. New release. Jan. 28, 2021. https://bit.ly/2NBiSrw).

In view of its wide spectrum of pharmacological properties, a procedure for large scale isolation of uttroside B and uttroside A is required to meet the industrial demand and is highly needed.

Moreover, all the reported methods in literature [Sharma, S. C et al., Phytochemistry. 1983, 22, 1241-1244; Guo, S-B et al., Asian Journal of Chemistry 2014, 26(15), 4615-4618; Nath, L. R et al., R. Scientific Reports 2016, 6, 36318] involved tedious steps for extraction, includes defatting of raw material with hexane followed by successive cold extraction thrice with MeOH, ethanol extracts and isolation of uttroside B involves several purification techniques viz., preparative TLC, ODS column chromatography, Sephadex LH-20 column chromatography and finally preparative HPLC.

These drawbacks prompted to find out a non-destructive method for the isolation of uttrosides, both A and B and develop an easy, economical process for the large scale isolation, so as to cater the needs for its possible clinical application.

DRAWBACKS OF PRIOR ART

Prior art processes for the isolation of uttrosides (both A & B) suffers from a number of disadvantages. The biggest disadvantage of prior art process is the lower yield of uttrosides (0.2%) when compared to the present method (0.6%). The second disadvantage of the reported method in prior art is the requirement of cold percolation process where, plant material is left over night in a solvent for each percolation, hence for complete extraction (twice with hexane, thrice with EtOAc and twice with MeOH) of plant material at least seven days are required. The third disadvantage of the above method is that it requires more solvent, more electricity, more manpower and more time, thus resulting in an expensive and time taking process for the isolation of uttroside A/B from the whole plant of *Solanum nigrum*. The fourth disadvantage of the reported process for the purification of uttroside A/B involves several steps of which, includes fractionation, repeated silica gel column chromatography purification, Sephadex LH-20 purification and final purification step involved preparative HPLC purification which are usually expensive and also required much longer times.

All the reported methods for the isolation of uttroside B and Uttroside A involved multi-step purification processes invariably including sephadex chromatography, and preparative HPLC purification as final resort to get pure compound. Use of HPLC purification rendered the processes un-economical, as the process is not extendable to kilograms scale. Hence the present invention provides of purification of uttroside A/B using a simple liquid-liquid extract, devoid of use of preparative HPLC purification step.

OBJECT OF THE INVENTION

The main object of the present invention is to provide an improved process for the isolation of uttroside B and uttroside A from whole plant of *Solanum nigrum.*

Another object of the present invention is to avoid use of tedious and time taking extraction and purification processes for the isolation of uttroside B (structure-1) and uttroside A (structure-2) from the whole plant of *Solanum nigrum*.

Structure 1

Uttroside B

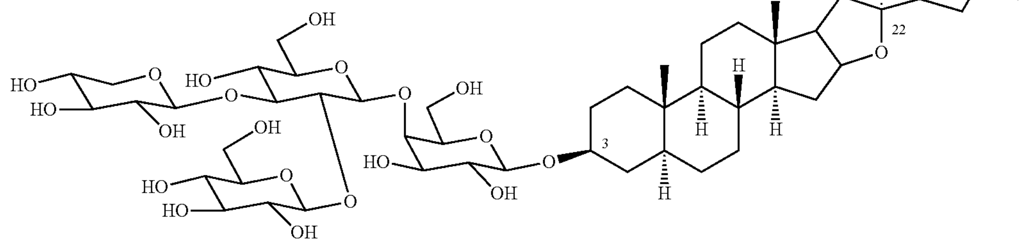

Structure 2

Uttroside A

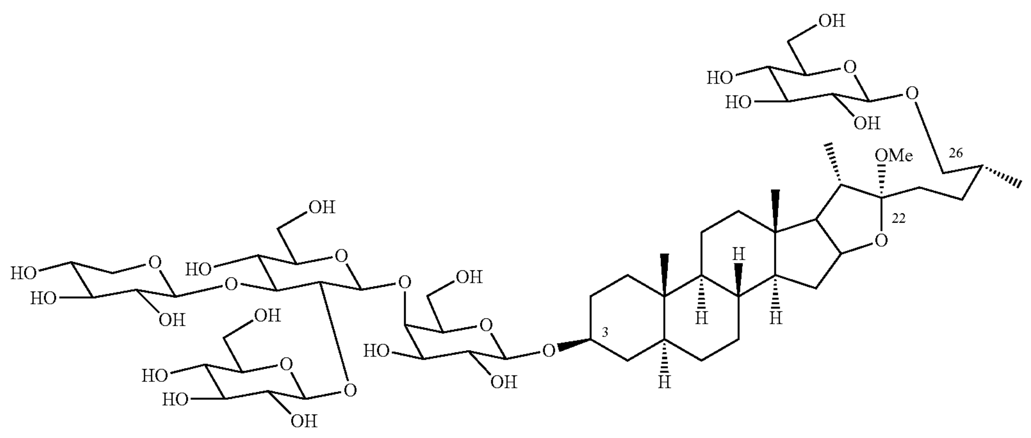

Still another object of the present invention is to provide an economical process for the isolation of uttroside B and uttroside A from the whole plant of *Solanum nigrum*.

Still another object of the invention is to provide a process that achieved complete extraction of plant material.

Still another object of the present invention is to provide a process that results in 0.6% yield of uttroside B and uttroside A.

A further objective of the present invention is to provide a process that uses 2-7 times lesser amount of solvents, electricity, manpower and time, in comparison to that of prior art isolation processes.

SUMMARY OF THE INVENTION

The present invention provides an improved process for the isolation of uttroside B and uttroside A from whole plant of *Solanum nigrum*, which comprises of drying, grinding and stirring of *Solanum nigrum* with 90% methanol at room temperature. Removal of solvents under vacuum at 35-40° C., precipitation and filtration of crude extracts to obtain uttroside B and uttroside A up to 0.5% and 0.1% of yields.

In an embodiment of the present invention, a varied ratios of solvents, viz., methanol, ethanol and water are used for the extraction of plant material.

In another embodiment of the present invention, complete extraction of plant material is achieved with mechanical stirring of plant material in the 90% methanol and 90% ethanol.

In yet another embodiment of the present invention, a varied ratios of ethanol, methanol, acetonitrile and acetone are used for precipitation.

In yet another embodiment of the present invention, the purification of uttroside B and uttroside A takes less time and is inexpensive.

In yet another embodiment of the present invention, the process results in 0.45-0.5% (w/w) yield advantage of uttroside B and 0.05-0.1% (w/w) uttroside A each to that of prior art process.

In yet another embodiment of the present invention the process uses 2-7 times lesser amount of solvents, electricity, manpower and time to that of prior art process.

DETAILED DESCRIPTION OF THE INVENTION

The invention will now be described in detail in connection with certain preferred and optional embodiments, so that various aspects thereof may be more fully understood and appreciated.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

The present disclosure is not to be limited in scope by the specific embodiments described herein, which are intended for the purposes of exemplification only. Functionally-equivalent products, compositions, and methods are clearly within the scope of the disclosure, as described herein.

Due to their special structural features, extraction, purification and isolation of saponins is a challenging task. In particular, uttroside B and uttroside A poses a serious challenge. Challenges associated with the extraction and isolation of saponins is essentially due to saponins, making it act like surfactant, arising from the presence of different functional groups e.g., OH, $CH_3$, or COOH, in the aglycone moiety. This is further complicated by the number, arrangement, and orientation of the sugar units, as well as the number and types of sugar chains attached to the aglycone moiety. In general, saponins have high polarity, chemically and thermally labile, non-volatile, and are usually found in low concentrations in plants (Li, B.: Abliz, Z.: Tang, M.: Fu, G.: Yu, S. J Chromatogr A 2006, 1101, 53-62). The fact that saponins occur in plants as a mixture of structurally similar compounds of similar polarity renders a challenge when it comes to separating them. No surprise therefore that in the isolation of these compounds, a number of different separation techniques, e.g., thin layer chromatography (TLC), column chromatography (CC), low pressure liquid chromatography (LPLC), medium pressure liquid chromatography (MPLC) and high performance liquid chromatography (HPLC), sephadex chromatography are usually used to affect complete separation and isolation of pure individual components. Conventional methods often fail to afford a pure uttroside from the complex mixture of saponins in natural extract of *Solanum nigrum*. All the reported methods for the isolation of uttroside B and uttroside A involve multi-step purification processes invariably including sephadex chromatography, and preparative HPLC purification as final resort to get pure compound.

The present invention provides relatively simple, efficient, solvent-economic, time-saving, scalable newer methods of purification of uttroside using a simple liquid-liquid extract, devoid of use of preparative HPLC purification step. The present invention adopted sequential liquid-liquid extraction/precipitation method to get rid of unwanted impurities such as chlorophyll, aminoacids, and other saponins preferentially by utilizing the differential polarity/partition of the targeted compound to get highly enriched product which has been finally subjected to reverse phase gravity chromatography for single step purification of uttroside A, B with >99% purity. Hence, the present invention is distinct and superior to the prior art isolation method. More importantly, the prior art method resulted in only 0.1% yield of uttroside B. Whereas in our method, a much higher yields of 0.45-0.5% of uttroside B could be obtained through a much simpler process protocol. The described method uses selective precipitation strategy for the isolation of uttroside A,B using a combination of common solvents such as methanol, ethanol, acetone completely obviating preparative HPLC step, making the process, simple, economical and industrially viable.

The present invention utilizes common extraction/chromatographic solvents such as methanol, ethanol, acetonitrile, acetone for preferential precipitation of impurities to enrich the product before taking up for the final reverse phase gravity chromatographic purification of uttroside A and uttroside B.

In an embodiment of the present invention, there is provided an improved process for the isolation of saponins, uttroside B and uttroside A from whole plant of *Solanum nigrum* comprising the steps of: (i) extracting air dried powdered whole plant of *Solanum nigrum* with an aqueous polar solvent containing 10-20% water; (ii) removing the aqueous polar solvent under vacuum at 35-40° C. to obtain a residue: (iii) diluting the residue with methanol or ethanol and removing the unwanted insoluble solid impurities by filtration to obtain a clear filtrate; (iv) repeatedly precipitating the filtrate to obtain a precipitate of dried enriched saponin fraction with uttroside A and uttroside B; and (v) subjecting the precipitate to reverse phase silica gel column chromatography to obtain both uttroside A and uttroside B in pure form.

In an embodiment of the present invention, there is provided an improved process for the isolation of saponins, uttroside B and uttroside A from whole plant of *Solanum nigrum* as disclosed herein, wherein the aqueous polar solvent used for extraction is selected from the group consisting of methanol and ethanol.

In an embodiment of the present invention, the repeated precipitation is carried out using a solvent selected from the group consisting of acetone, acetone-methanol, and acetone-ethanol. In another embodiment of the present invention, the repeated precipitation is carried out by dissolving the dried enriched saponin fraction in a solvent selected from methanol or ethanol followed by addition of acetone under stirring condition.

In an embodiment of the present invention, the gradient mixture used to elute in reverse phase column chromatography is methanol-water or acetonitrile-water.

In an embodiment of the present invention, the yield of pure uttroside B is 0.45-0.5% and uttroside A is 0.05-0.1%. In another embodiment of the present invention, the uttorside A and uttroside B are interconvertible.

In an embodiment of the present invention, the entire process of isolation is carried out within 48 hours which include extraction, precipitation and reverse phase column chromatographic purification of uttrosides, both A and B.

In an embodiment of the present invention, the mixture of uttroside A and uttroside B was refluxed in water for 48 hours to afford uttroside B. In another embodiment of the present invention, the mixture of uttroside B and uttroside A was refluxed in methanol in the presence of 1% silica gel to afford uttroside A.

The embodiments of the present invention will be more specifically explained by following examples. However, the following examples are given by way of illustration and the scope of the present invention is not limited to the scope of these examples.

EXAMPLES

Example 1

Air dried powdered whole plant of *Solanum nigrum* (1 kg) was stirred with aqueous methanol (containing 10-20% water, 3 Litres) at RT for 24 hours. Plant material was filtered off and the filterate was concentrated in vacuo. The residue obtained was diluted with equal volume (vs weight of residue) of methanol and stirred for 30 minutes and the insoluble solid was removed by filtration. The clear methanolic filtrate was added drop wise to acetone (300 ml) with stirring and the resulting precipitated solid was separated by filtration. The solid residue obtained was dissolved in minimum volume of methanol (30 ml) followed by addition of acetone (300 ml) under stirring condition. The precipitated saponins filtered and loaded on RP18 silica gel column (70 mm diameter, 480 mm height) and eluted with gradient mixture of methanol-water. Upon concentration of the eluted fraction (MeOH:$H_2O$: 60:40), yielded pure uttroside B (0.5%) and uttroside A (0.1%) as white amorphous solids.

Example 2

Air dried powdered whole plant of *Solanum nigrum* (1.0 kg) was stirred with aqueous ethanol (containing 10-20% water, 3 litres) at RT for 24 hours. Plant material was filtered off and the filterate was concentrated in vacuo. The residue obtained was diluted with equal volume (vs. weight of residue) of ethanol and stirred for 30 minutes and the insoluble solid was removed by filtration. The residue obtained upon repeated precipitation with acetone-ethanol (1:1) mixture and filtration (thrice) resulted in the isolation of uttroside enriched saponin fraction which upon RP18 silica gel column chromatography with gradient mixture of methanol-water (60:40), afforded uttroside B (0.45%) and uttroside A (0.05%) as white amorphous solids.

Example 3

Air dried powdered whole plant of *Solanum nigrum* (1 kg) was stirred with aqueous methanol (containing 10-20% water, 3 litres) at RT for 24 hours. Plant material was filtered off and the filtrate was concentrated in vacuo. The residue obtained was diluted with equal volume (vs. weight of residue) of methanol and stirred for 30 minutes and the insoluble solid was removed by filtration. The clear methanolic filtrate was added drop wise to acetone (300 ml) with stirring and the resulting precipitated solid was separated by filtration. The solid residue obtained was dissolved in minimum volume of methanol (30 ml) followed by addition of acetone (300 ml) under stirring condition. The precipitated saponins filtered and loaded on RP18 silica gel column (70 mm diameter, 480 mm height) and eluted with gradient mixture of acetonitrile-water. Upon concentration of the eluted fraction ($CH_3CN$:$H_2O$: 50:50), yielded pure uttroside B (0.5%) and uttroside A (0.1%) as white amorphous solids.

Example 4

Air dried powdered whole plant of *Solanum nigrum* (1.0 kg) was stirred with aqueous ethanol (containing 10-20% water, 3 Litres) at RT for 24 hours. Plant material was filtered off and the filtrate was concentrated in vacuo. The residue obtained was diluted with equal volume (vs. weight of residue) of ethanol and stirred for 30 minutes and the insoluble solid was removed by filtration. The residue obtained upon repeated precipitation with acetone-ethanol mixture (1:1) and filtration (thrice) resulted in the isolation of uttroside enriched saponin fraction which upon RP18 silica gel column chromatography with gradient mixture of acetonitrile-water (50:50), afforded uttroside B (0.45%) and uttroside A (0.05%) as white amorphous solids.

The uttorside A and uttroside B are interconvertible. The mixture of uttroside A and uttroside B was refluxed in water for 48 hours to afford uttroside B. The mixture of uttroside B and uttroside A was refluxed methanol in the presence of 1% silica gel to afford uttroside A as depicted in interconversion of uttrosides A, B scheme 1 below.

Scheme 1

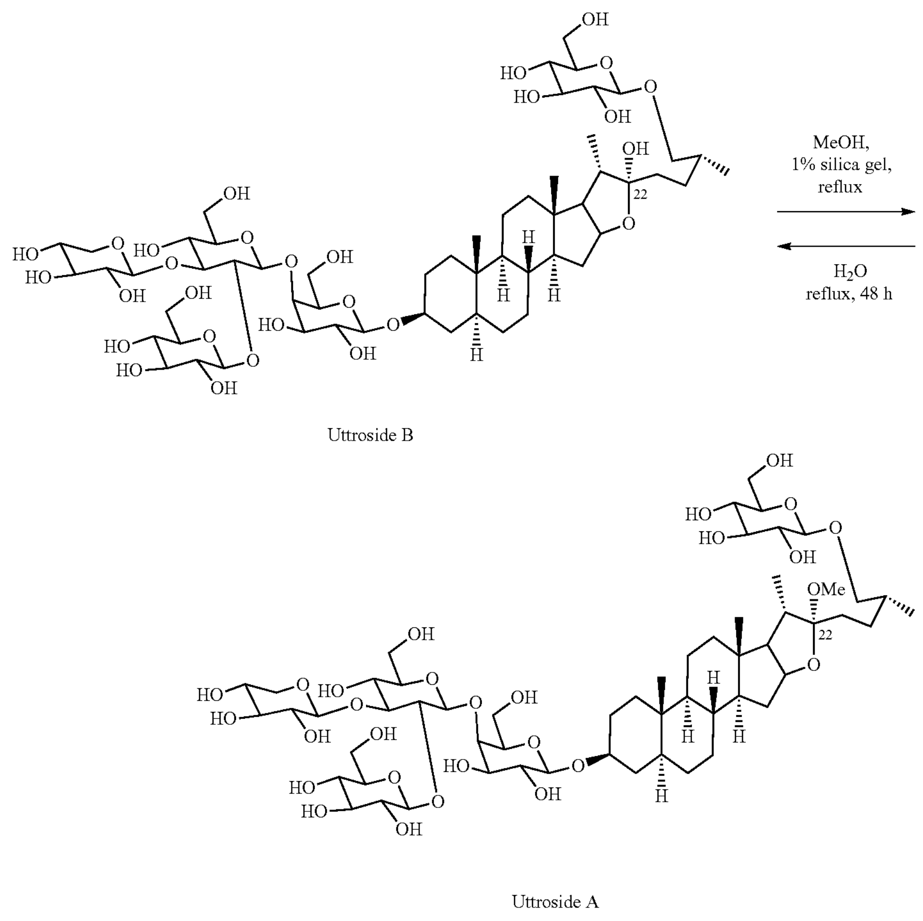

Uttroside B

Uttroside A

ADVANTAGES

1. The present process uses simple precipitation and filtration methods for the isolation and purification of uttroside B and uttroside A, from *Solanum nigrum*, which are easy, less time taking and inexpensive.

2. The other major advantage of the present process is that without using of hot Soxhlet extraction, defatting and complete extraction of the plant material is achieved in only one day using single solvent with mechanical stirring.

3. The main advantage of the present process is that it results in 0.5% (w/w) yield advantage of uttroside B and 0.1% of uttroside A to that of prior art process.

4. The other advantages of our process are that it uses 2-7 times less amount of solvents, electricity, manpower and time to that of prior art process.

We claim:

1. An improved process for the isolation of saponins, uttroside B and uttroside A from whole plant of *Solanum nigrum* comprising the steps of:

(i) extracting air dried powdered whole plant of *Solanum nigrum* with an aqueous polar solvent containing 10-20% water;

(ii) removing the aqueous polar solvent under vacuum at 35-40° C. to obtain a residue;

(iii) diluting the residue with methanol or ethanol and removing the unwanted insoluble solid impurities by filtration to obtain a clear filtrate;

(iv) repeatedly precipitating the filtrate to obtain a precipitate of dried enriched saponin fraction with uttroside A and uttroside B; and (v) subjecting the precipitate to:

(a) reverse phase silica gel column chromatography to obtain both uttroside A and uttroside B in pure form; or (b) refluxing in water for 48 hours to afford the uttroside B; or (c) refluxing in methanol in the presence of 1% silica gel to afford uttroside A.

2. The process as claimed in claim 1, wherein the aqueous polar solvent used for extraction is selected from the group consisting of methanol and ethanol.

3. The process as claimed in claim 1, wherein repeated precipitation is carried out using a solvent selected from the group consisting of acetone, acetone-methanol, and acetone-ethanol.

4. The process as claimed in claim 1, wherein the repeated precipitation is carried out by dissolving the dried enriched saponin fraction in a solvent selected from methanol or ethanol followed by addition of acetone under stirring condition.

5. The process as claimed in claim 1, wherein the precipitate subjected to the reverse phase silica gel column chromatography is subjected to a mixture of methanol-water or acetonitrile-water.

6. The process as claimed in claim 5, wherein the yield of pure uttroside B is 0.45-0.5% and uttroside A is 0.05-0.1%.

7. The process as claimed in claim 5, wherein the entire process of isolation is carried out within 48 hours.

8. The process as claimed in claim 1, wherein the precipitate of dried enriched saponin fraction with uttroside A and uttroside B is refluxed in water for 48 hours to afford the uttroside B.

9. The process as claimed in claim 1, wherein the precipitate of dried enriched saponin fraction with uttroside B and uttroside A is refluxed in methanol in the presence of 1% silica gel to afford uttroside A.

* * * * *